United States Patent

Schiavo

[11] Patent Number: 5,147,288
[45] Date of Patent: Sep. 15, 1992

[54] COTTON SWAB WITH DEPTH PREVENTION MECHANISM

[75] Inventor: Pietro Schiavo, Chiuppano, Italy

[73] Assignee: Ivalda S.P.A., Chiuppano, Italy

[21] Appl. No.: 709,160

[22] Filed: Jun. 3, 1991

Related U.S. Application Data

[63] Continuation of Ser. No. 185,961, Apr. 25, 1988.

[51] Int. Cl.$^5$ .............................................. A61M 35/00
[52] U.S. Cl. .......................................................... 604/1
[58] Field of Search ....................................... 604/1-3, 604/54, 328, 385.1, 904; 606/131; 15/210 R

[56] References Cited

U.S. PATENT DOCUMENTS

| | | | |
|---|---|---|---|
| 2,510,961 | 6/1950 | Davis | 604/1 |
| 2,876,501 | 3/1959 | Glickson | 604/1 |
| 3,881,464 | 5/1975 | Levene | 604/1 X |
| 4,804,362 | 2/1989 | Enzo | 604/1 |
| 4,820,259 | 4/1989 | Stevens | 604/1 |
| 4,883,454 | 11/1989 | Hamburg | 604/1 |
| 4,887,994 | 12/1989 | Bedford | 604/1 |
| 4,902,275 | 2/1990 | Fassbind | 604/1 |
| 4,935,001 | 6/1990 | George | 604/1 |

FOREIGN PATENT DOCUMENTS

| | | | |
|---|---|---|---|
| 0089271 | 9/1983 | European Pat. Off. | 604/1 |
| 0120235 | 10/1984 | European Pat. Off. | 604/1 |
| 0234061 | 5/1987 | European Pat. Off. | 604/1 |
| 0237589 | 9/1987 | European Pat. Off. | 604/1 |

Primary Examiner—C. Fred Rosenbaum
Assistant Examiner—Mark O. Polutta
Attorney, Agent, or Firm—Eugene E. Renz, Jr.

[57] ABSTRACT

A cotton swab, comprising: an ear canal engaging portion of a small enough diameter to fit within and clean the inside surface of an ear canal, an adjacently located ear cavity engaging portion of greater diameter than the ear canal within which the cotton swab is intended to be used, and a stick securely holding the ear canal and ear cavity engaging portions, the stick having a longitudinal axis, the ear cavity engaging portion having a gradual sloping interface surface which is non-perpendicular to the axis of the stick and having a variable diameter and providing a smooth contour directly connected to the ear canal engaging portion, the ear cavity engaging portion comprising a first section incrementally increasing in dimension and located adjacent to the interface surface and a second section incrementally decreasing in dimension and located distally from the ear canal engaging portion, the first and seconds being substantially symmetrical to one another about an axis perpendicular to the longitudinal axis of the stick, the ear cavity enlarging portion serving to prevent depth penetration of the ear canal engaging portion beyond a predetermined length and at the same time providing a surface for cleaning that portion of an ear cavity adjacent to the ear canal and other portions of the ear cavity as the cotton swab is moved within the ear canal.

4 Claims, 2 Drawing Sheets

COTTON SWAB WITH DEPTH PREVENTION MECHANISM

This is a continuation of my co-pending patent application Ser. No. 07/185,961 filed Apr. 25, 1988 pending.

FIELD OF THE INVENTION

The present invention relates to a cotton swab which is intended for use in cleaning ears, both the external and internal portions of the outer ear and, to some degree, a slight, but not insignificant internal portion of the auditory canal or the ear canal. Preferably, the cotton swab is to be used by parents for cleaning the ears of their young children and particularly infants. The cotton swab is also intended to be used by individuals on their own ears.

BACKGROUND OF THE INVENTION

The prior art devices teach a variety of tip shapes for cotton swabs useful in cleaning the external cavity and internal canal of the human ear. Generally, however, the shapes of the prior art are of the elongated teardrop configuration and it is presently understood that the outer diameter of the cotton swabs, so shaped, is less than the expected internal diameter of the auditory canal, so that the cotton swabs can be fully inserted into the ear. This however, creates the real possibility, indeed, high probability, that actual temporary or permanent damage, or at the least, long or short enduring pain, results. These shapes, however, fail to teach or suggest the unique and highly advantageous shaped tip of the cotton swab of the present invention.

More specifically, there is neither a teaching nor a suggestion in the prior art of providing a cotton swabbed tip of a cotton swab with a cylindrical, forwardly protruding, canal-insertable tip portion which is adjacent to and enlarges into a bulbous ear cavity surface-engaging portion to effectively, simultaneously, clean both the ear cavity and a not insignificant depth of the ear canal and, yet, also prevents accidental depth penetration into the ear canal beyond a predetermined maximum amount. The prior art, in fact, seems totally devoid of any appreciation of providing a shaped tip of a cotton swab which provides for a predetermined maximum degree or measure of depth penetration into the ear canal, with safety. Furthermore, the prior art fails to teach or suggest a tip of a cotton swab which simultaneously cleans both the outer ear cavity and a portion of the ear canal by mere rotation of the cotton swab about the longitudinal axis of the stick. The prior art also fails to teach or suggest a tip of a cotton swab which positively prevents the user from thrusting or pushing the tip of the cotton swab beyond the predetermined limit of safety of penetration.

The cotton-swabbed tip of the device is provided with a shaped surface which prevents the user from accidentally or inadvertently forcing the tip too far into the ear canal of the individual whose ear is then being cleaned. Thus, a depth prevention mechanism is provided to the tip of the cotton swab and this serves to protect the ear's structure, especially the middle ear components including the ear drum membrane. It also eliminates the pain and discomfort otherwise associated with cleaning ears and avoids the feeling of anxiety of those individuals who are having their ears cleaned by others as well as the anxiety felt by the individual who is actually doing the ear cleaning to another. It is a definite need, concern and problem, especially to parents, to clean the ears of newborns, infants, and young children with cotton swabs and, yet, the parents are hesitant to do so because of the potential of going into the ear canal too deeply and thereby causing permanent or temporary damage to the components of the middle ear. Some parents are not appreciative of the risk of going into the ear cavity too deeply and they can easily cause permanent damage to the child's middle ear structure, the ear drum, etc. because they do not recognized the maximum depth of penetration which, if exceeded, can cause pain or damage to the ear structure.

The present invention provides a unique and highly advantageous leading surface for the cotton-swabbed tip of the cotton swabs. The design of the tip prevents accidental penetration beyond the maximum safety limit. In this manner, the parents can easily and efficiently clean their children's ears without worrying about going into the ear canal too deeply. Furthermore, the shape of the cotton-swabbed tip enables effective simultaneous cleaning of a not insignificant outer portion of the ear canal and the outer ear, or ear cavity, by providing, in the first instance a cotton surface of smaller dimension than the diameter of the auditory canal and, for the outer ear, by providing a cotton swabbed smooth surface which, during use, abuts against the ear cavity. Therefore, the cotton swab effects efficient cleaning of the ear cavity and ear canal, while ensuring that the cotton swab does not, however, penetrate into the ear canal beyond the predetermined maximum safety limit.

The cotton swab with the depth prevention mechanism is, of course, not only for use by parents with respect to the ears of the children but, as mentioned, in addition, it can be used with effectiveness by an individual with respect to cleaning one's own ears. Here again, the shaped tip surface of the cotton swab allows for a certain degree of ear canal depth penetration so cleaning of the ear canal and cavity is accomplished and, yet, the cotton swab cannot be pushed into the ear canal too far, so as to damage the middle ear or its components, and thereby cause permanent damage, tearing of the eardrum, or, at the least, immediate discomfort.

SUMMARY OF THE INVENTION

The present invention relates to a new cotton swabbed tip shape of a cotton swab which facilitates the efficient cleaning of the outermost portion of the ear canal and the inside portion of the ear cavity and, yet, prevents the tip of the cotton swab from being pushed into the ear canal too deeply so as to damage the middle ear components and/or cause temporary or permanent pain or discomfort. In the preferred embodiment of the present invention, the shaped tip portion of the cotton swab is provided on both ends of the cotton swab. However, for purposes of the present description of the invention, only one tip will be described, it being appreciated by those of ordinary skill in the art to which the present invention pertains, that both ends of the cotton swab can, if desired, be provided with the same shape or, alternatively, the ends of the cotton swab can be dissimilar from one another to provide a bit more functional versatility to the cotton swab. That, of course, is a marketing decision, better made by the manufacturers and ultimate consumers of the product.

A cotton swab is provided with a shaped tip intended to be used for cleaning ears and particularly children's and infant's ears. The cotton swab is provided with a maximum depth prevention mechanism which allows for some limited cleaning of the auditory canal, hereinafter referred to as the ear canal, and the inner surface of the outer ear, hereinafter referred to as the ear cavity without fear of penetrating into the ear canal too deeply so as to cause discomfort or damage to the middle or inner ear structure. The cotton swab has a shaped, cotton tip surface to prevent inadvertent damage to the interior of the ear. According to the preferred embodiment, the leading portion of the cotton tip of the cotton swab is cylindrical and of a dimension so as to be insertable into the ear canal. It is followed by, and is adjacent to, a larger dimensioned, sphere or bulbous cotton portion, which during use will abut against the ear cavity. To use a cotton swab, after insertion into the ear, the swab is rotated about the longitudinal axis of the cotton swabbed stick. The tip simultaneously cleans the ear, canal and ear cavity surface and, yet, the depth prevention mechanism, the bulbous cotton portion adjacent to the cylindrical tip prevents the ear canal portion from being inserted farther than the predetermined maximum safety limit.

The preferred embodiment of the present invention is a cotton swab which is provided on both of its ends with a shaped cotton swabbed tip which enables efficient cleaning of the visible surface of the ear cavity and the outermost portion of the ear canal and, yet, the shape of the tip of the cotton swab is such that accidental and inadvertent further penetration into the ear canal beyond the predetermined safety limit is prevented. This is accomplished, accordingly to the preferred embodiment of the present invention, by providing the stick of the cotton swab with fibrous cotton, shaped, on its ends, in a configuration such that the leading tip of the cotton coated swab stick is of a conical, preferably cylindrical profile, of external diameter less than the internal diameter of the ear canal within which the swab is intended to be used, such that it can easily be placed into the ear canal and provide efficient cleaning of the interior wall surface of the ear canal. The cleaning action is, of course, accomplished by rotation of the swab about the longitudinal axis of the stick while simultaneously pushing the swab into and withdrawing the stick from the ear. Rotation of the swab about its longitudinal axis, i.e. about its stick axis also, simultaneously causes the bulbous, preferably spherically shaped, cotton swabbed portion, adjacent to the leading end of the swab, i.e., the cylindrical portion of smaller diameter, to simultaneously clean the outer ear surface. The spherical, adjacently located, cotton swab portion of increased dimension, vis a vis, the diameter of the cylindrical or leading portion of the swab prevents the tip of the cotton swab from being forced further into the ear canal than the predetermined safety limit, since the spherical portion of the tip will encounter and be held against the surface of the outer ear cavity. In this manner, the tip of the cotton swab cannot be forced into the ear canal beyond the safety depth of penetration, equal to the length of the leading cylindrical portion of the tip.

Other shapes can, of course, be used to accomplish the proposes sought to be accomplished by the present invention. For example, the leading tip portion can taper from the bulbous portion towards its tip and the maximum depth prevention mechanism the bulbous portion (immediately behind, yet, adjacent to the tip) being spherical, diamond shaped (in cross section) or even "donut-shaped" (when viewed from a side). Also, while it is presently contemplated that the leading edge of the tip of the cotton swab is substantially flat, it is also within the contemplation of the present invention that the leading edge of the tip can be slightly curved so as to provide some additional comfort to the ear, during insertion.

The principal aspect of the present invention, however, is the provision of a cotton swabbed tip of a cotton swab of dimensions such that a portion can easily be inserted into the ear canal of the individual whose ear is being cleaned. The tip portion is located at the distal end of the stick and adjacent to a cotton swabbed portion of the stick of greater width or diameter dimensions than the ear canal but, nevertheless, its diameter or width is less than the ear opening. In this manner, the tip of the cotton swab can be inserted into and clean the outermost portion of the auditory canal and simultaneously clean the surface of the cavity (with the enlarged or bulbous portion of the cotton swab abutting against the ear cavity). The greater dimensioned width or diameter of the bulbous portion of the cotton swab, as mentioned, positively prevents accidental and inadvertent depth penetration beyond the predetermined critical amount.

BRIEF DESCRIPTION OF THE DRAWINGS

These and other objects of the present invention and the various features and details of the operation and construction thereof are hereinafter more fully set forth with reference to the accompanying drawings, where.

DETAILED DESCRIPTION OF THE PREFERRED EMBODIMENT

Figure 2:
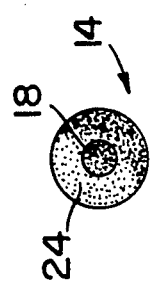
FIG. 2 is a side plan view of the preferred embodiment of the invention shown in FIG. 1.

A cotton swab 10, generally shown in all of the drawings, comprises a stick portion 12, which, according to current manufacturing and safety specifications, is hollow and made from a flexible plastic material. At each end of the stick portion 12, an ear cleaning section 14 is provided. As previously mentioned, it is within the scope of the present invention that only one end of the stick portion can be provided with the ear cleaning section 14, the other end can either have a different configuration, for a different purpose, or the same configuration thereby providing a cotton swab, both ends of which can be used before discarding. That, as mentioned, is a decision to be made by the manufacturer and distributor, based on marketing and customer acceptance consideration.

The ear cleaning section 14 is coated, preferably by gluing, with strands of cotton fibrous material, in a well known manner. However, according to the present invention, an ear canal engaging portion 18 of the cotton swab 10, i.e. the end 16 (not shown) of the stick portion 12, is coated basically, conical, in the preferred embodiment, cylindrical. The front edge 22 is substantially flat although it should appreciated that it can be slightly curved, to facilitate ease of insertion into the ear. The ear canal engaging portion 18 is adjacent to a depth preventing mechanism 24, which according to the preferred embodiment of the present invention, is spherically shaped but represents a continuous cotton wrapped portion of the cotton swab. Here, again, it should be appreciated that it is within the scope of the present invention for the depth preventing mechanism 24 to be any conical or other shape so long as the ear cavity engaging portion 26 (the part of the depth preventing mechanism 24 which actually contacts the outer ear of the user, during use of the cotton swab) is wider than the diameter of the ear canal section of the ear of the person whose ear is to be cleaned.

Figure 5:
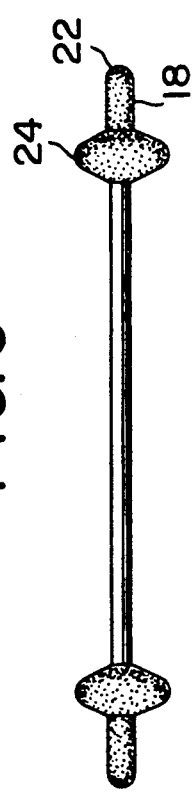
FIG. 5 is a front plan view of a third shape embodiment of the invention, this cotton swab having a cylindrical shaped, with curved, not flat, leading edge, an ear canal portion and a smooth curved diamond shaped (in cross section) ear cavity engaging portion.
Figure 7:
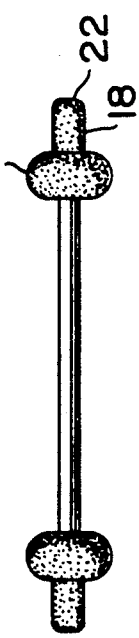
FIG. 7 is a front plan view of a fourth shape embodiment of the invention, this cotton swab having a cylindrical ear canal portion and a donut shaped (in side view) ear cavity engaging portion.

In other embodiments of the invention the depth preventing mechanism 24 is donut-shaped (when viewed from the end of front edge 22 of the cotton swab) (as shown in FIG. 7) or diamond shaped with smooth curved walls (when the cotton swab is viewed from the front) (as shown in FIG. 5). Indeed, it should be appreciated that may different shapes were originally selected for trial use and the shape that received the most favorable reception by pediatricians, hospitals and clinics was selected as the preferred embodiment. Also, as mentioned, the ear canal engaging portion 18, i.e., the portion that is intended to be inserted into the ear canal, can be tapered from the end of the ear cavity engaging portion 26 toward the front edge 22.

According to the preferred embodiment of the present invention, the cotton used for manufacturing the cotton swabs is 100% pure cotton. The sticks are made from polypropylene, obtainable from BASF of Montedison. The cotton is sealed or adhered to the sticks with a combination of water, glue and an anti-molding composition (to prevent fungus type mold from cultivating) all which is melted and molded onto the tips 20 of the stick portion 12. The tip shape of the cotton swab, comprising the ear cleaning section 14, is accomplished by simple machine molding or other conventional shaping techniques.

According to the preferred embodiment of the present invention, the stick length of a cotton swab, which is provided on both ends with an ear canal engaging portion 18 and a depth preventing mechanism 24, is about 73 mm. The distance between the near ends of the depth preventing mechanism 24, in the preferred embodiment comprising spheres, is about 45.5 mm. The diameter of the spheres or depth preventing mechanisms 24 is about 10 mm, and the distance from far end to far end of the two spheres is about 64.5 mm. The overall length of the cotton swab is about 78.5 mm. This, then, dictates an individual length of a single ear canal engaging portion of about 7 mm with the length of an ear cleaning section 14 being about 16.5 mm. The diameter of the cylindrical ear canal engaging portion 18 of the cotton swab 10 is preferably about 5.5 mm. This constitutes about 2.7 mm of stick outside diameter with the balance being cotton material encircling the stick portion 12.

It has been determined that these dimensions allow for superior ear canal cleaning in that the 5.5 mm dimension of the ear canal engaging portion 18 is easily capable of being inserted into an ear canal of even small infants and yet, the 10 mm diameter of the depth preventing mechanism 24. In this embodiment the spheres, is larger than the anticipated actual ear canal diameter and, therefore, the bulbous or depth preventing mechanism 24 of the cotton swab 10 cannot be inserted into the ear canal beyond the point of contact between the ear cavity-engaging portion and the ear cavity or the surface of the outer ear. This, then, only allows the cylindrical portion of the cotton swab, the ear canal engaging portion 18, to be inserted into the ear canal a distance about equal to 7 mm, a depth which cannot cause temporary or permanent damage and will not even cause temporary discomfort or pain.

The cotton swab 10, when inserted into the ear, will have the ear canal engaging portion 18 located within the ear canal, i.e., the auditory canal. The depth of penetration, however, will be sufficiently deep so as to allow for cleaning of the outer portion of the ear canal, but it will be prevented from being inserted or pushed deeper than the maximum safety limit of penetration by the abutment between the ear cavity-engaging portion 26 with the ear cavity of the ear, i.e. the outer ear surface. Cleaning of the ear canal and the ear cavity, simultaneously, is provided by turning the cotton swab about the longitudinal axis of the stick portion 12, while simultaneously pushing and pulling the ear cleaning section 14 with respect to the ear. Thus, a device is provided which cleans both the ear canal and ear cavity, at the same time, and, in addition, the cotton swab is positively prevented from being thrust or pushed into the auditory canal a depth which would cause damage and/or pain.

According to other dimensional and shape embodiments of the present invention, the following dimensions for the illustrated shapes were found to be successful in accomplishing the desired purpose, yet were not found to be quite as acceptable as the preferred embodiments's shape and dimensions, for a variety of reasons.

Figure 1:
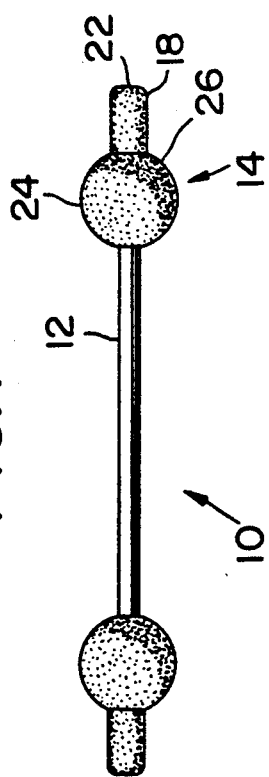
FIG. 1 is a front plan view of the preferred embodiment of the present invention.

FIRST SHAPE EMBODIMENTS (FIGS. 1 and 2). SECOND SET OF DIMENSIONS

Stick length: 82 mm
Overall Length: 90 mm
Far end of sphere to far end of other sphere: 73 mm
Near end of sphere to near end of other sphere: 50 mm
Stick Diameter: 2.7 mm
Diameter of Ear Canal Engaging Portion: 5.0 mm
Diameter of Ear Cavity Engaging Portion (Sphere): 12 mm
Length of Ear Canal Engaging Portion: 8.5 mm FIRST SHAPE EMBODIMENTS (FIGS. 1 and 2), THIRD SET OF DIMENSIONS Stick Length: 64 mm
Overall Length: 70 mm
Far end of sphere to far end of other sphere: 54 mm
Near end of sphere to near end of other sphere: 40 mm
Stick Diameter: 2.7 mm
Diameter of Ear Canal Engaging Portion: 4 mm Diameter of Ear Cavity Engaging Portion (Sphere): 8 mm Length of Ear Canal Engaging Portion: 8 mm

Figure 4:
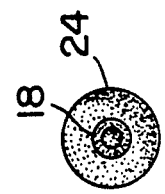
FIG. 4 is a side plan view of the embodiment shown in FIG. 3.
Figure 3:
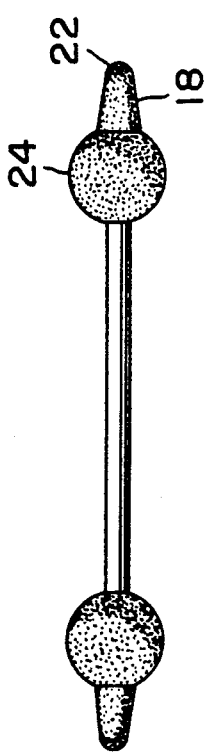
FIG. 3 is a front plan view of a second shape embodiment of the invention, this cotton swab having a tapered ear canal portion and a spherical ear cavity-engaging portion.

SECOND SHAPE EMBODIMENT (FIGS. 3 and 4), FIRST SET OF DIMENSIONS

Stick Length: 80 mm
Overall Length: 90 mm
Far end of sphere to far end of other sphere: 76 mm
Near end of sphere to near end of other sphere: 50 mm
Stick Diameter: 2.7 mm
Smallest Diameter of Ear Canal Engaging Portion: 3 mm
Largest Diameter of Ear Canal Engaging Portion (Adjacent to the Ear Cavity Engaging Portion: 5 mm
Diameter of Ear Cavity Engaging Portion (Sphere): 12 mm
Length of Ear Canal Engaging Portion: 7 mm

SECOND SHAPE EMBODIMENT (FIGS. 3 and 4), SECOND SET OF DIMENSIONS

Stick Length: 70 mm
Overall Length: 80 mm
Far end of sphere to far end of other sphere: 66 mm
Near end of sphere to near end of other sphere: 46 mm
Stick Diameter: 2,7 mm
Smallest Diameter of Ear Canal Engaging Portion: 3 mm
Largest Diameter of Ear Canal Engaging Portion (Adjacent to the Ear Cavity Engaging Portion): 5 mm
Diameter to Ear Cavity Engaging Portion (Sphere): 10 mm
Length of Ear Canal Engaging Portion: 7 mm

SECOND SHAPE EMBODIMENT (FIGS. 3 and 4), THIRD SET OF DIMENSIONS

Stick Length: 60 mm
Overall Length: 70 mm
Far end of sphere to far end of other sphere: 56 mm
Near end of sphere to near end of other sphere: 40 mm
Stick Diameter: 2.7 mm
Smallest Diameter of Ear Canal Engaging Portion: 2 mm
Largest Diameter of Ear Canal Engaging Portion (Adjacent to the Ear Cavity Engaging Portion): 5 mm
Diameter to Ear Cavity Engaging Portion (Sphere): 8 mm
Length of Ear Canal Engaging Portion: 7 mm

Figure 6:
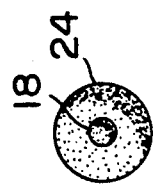
FIG. 6 is a side plan view of the embodiment shown in FIG. 5.

THIRD SHAPE EMBODIMENT (FIGS. 5 and 6), FIRST SET OF DIMENSIONS

Stick Length: 89 mm
Overall Length: 95 mm
Far end of Diamond Shape to far end of other Diamond Shape: 77 mm
Near end of Diamond Shape to near end of other Diamond Shape: 65 mm
Stick Diameter: 2.7 mm
Diameter of Ear Canal Engaging Portion: 4 mm
Maximum Diameter of Ear Cavity Engaging Portion: 12 mm
Length of Ear Canal Engaging Portion: 9 mm

THIRD SHAPE EMBODIMENT (Second Set of Dimensions)

Stick Length: 75 mm
Overall Length: 80 mm
Far end of Diamond Shape to far end of other Diamond Shape: 66 mm
Near end of Diamond Shape to near end of other Diamond Shape: 56 mm
Stick Diameter: 2.7 mm
Diameter of Ear Canal Engaging Portion: 4 mm
Maximum Diameter of Ear Cavity Engaging Portion: 10 mm
Length of Ear Canal Engaging Portion: 7 mm

Figure 8:
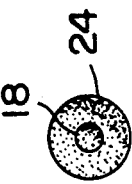
FIG. 8 is a side plan view of the embodiment shown in FIG. 7.

FOURTH SHAPE EMBODIMENT (FIGS. 7 and 8)

Stick Length: 64 mm
Overall Length: 70 mm
Far end of Donut Shape to far end of other Donut Shape: 56 mm
Near end of Donut Shape to near end of other Donut Shape: 46 mm
Stick Diameter: 2.7 mm
Diameter of Ear Canal Engaging Portion: 4 mm
Diameter of Ear Cavity Engaging Portion Donut: 10 mm
Length of Ear Canal Engaging Portion: 7 mm It should be appreciated that the scope of the present invention is not limited to the drawings illustrated or described herein. Rather, it should be understood that the specific forms of the invention herein illustrated and described are intended to be representative only, as certain changes may be made therein without departing from the clear teachings of the disclosure. Accordingly, reference should be made to the following appended claims, as interpreted by the Courts, in determining the full scope of the invention.

What is claimed is:

1. A cotton swab, comprising: an ear canal engaging portion of a small enough diameter to fit within and clean the inside surface of an ear canal and having a substantially uniform diameter over its length with a substantially flat terminal end, an adjacently located ear cavity engaging portion of greater diameter than said ear canal within which said cotton swab is intended to be used, and a stick securely holding said ear canal and ear cavity engaging portions, said stick having a longitudinal axis, said ear cavity engaging portion having a gradual sloping interface surface which is non-perpendicular to said axis of said stick and providing a smooth contour directly connected to said ear canal engaging portion, said ear cavity engaging portion comprising a first section incrementally increasing in dimension from said interface surface to a maximum diameter and a second section incrementally decreasing in dimension from said maximum diameter and located distally from said ear canal engaging portion to provide and axial length of said ear canal engaging portion which is no greater than said maximum diameter, said first and second section being substantially symmetrical to one another about an axis perpendicular to said longitudinal axis of said stick, said ear cavity engaging portion serving to prevent depth penetration of said ear canal engaging portion beyond a predetermined length and at the same time providing a surface for cleaning that portion of an ear cavity adjacent to the ear canal and other portions of said ear cavity as said cotton swab is moved within said ear canal, said second section of said ear cavity engaging portion also providing a surface for cleaning those portions of the ear cavity which can not be reached by said first section due to the interference of said ear canal engaging portion extending therefrom.

2. A cotton swab as claimed in claim 1 wherein said ear cavity engaging portion is in the shape of a donut or a diamond.

3. A cotton swab as claimed in claim 1 wherein the ratio of the largest diameter of said ear cavity engaging portion to the largest diameter of said ear canal engaging portion is substantially 3:1.

4. A cotton swab as claimed in claim 1 wherein said ear canal engaging portion is basically conical and tapered down from said interface surface of said ear cavity engaging portion to the far edge of said ear canal engaging portion.

* * * * *